US009494469B2

(12) United States Patent
Yon et al.

(10) Patent No.: US 9,494,469 B2
(45) Date of Patent: Nov. 15, 2016

(54) INFRARED DETECTION DEVICE

(71) Applicants: COMMISSARIAT A L'ENERGIE ATOMIQUE ET AUX ENE ALT, Paris (FR); ULIS, Veurey-Voroise (FR)

(72) Inventors: Jean-Jacques Yon, Sassenage (FR); Emmanuel Bercier, Noyarey (FR)

(73) Assignees: Commissariat à l'énergie atomique et aux énergies alternatives, Paris (FR); ULIS, Veurey-Voroise (FR)

( * ) Notice: Subject to any disclaimer, the term of this patent is extended or adjusted under 35 U.S.C. 154(b) by 227 days.

(21) Appl. No.: 14/105,663

(22) Filed: Dec. 13, 2013

(65) Prior Publication Data
US 2015/0316472 A1 Nov. 5, 2015

(30) Foreign Application Priority Data

Dec. 17, 2012 (FR) ...................... 12 62132

(51) Int. Cl.
| | |
|---|---|
| *G01N 21/00* | (2006.01) |
| *G01J 5/04* | (2006.01) |
| *G01N 21/3504* | (2014.01) |
| *G01J 3/42* | (2006.01) |

(Continued)

(52) U.S. Cl.
CPC ............... *G01J 5/041* (2013.01); *G01J 3/42* (2013.01); *G01J 5/0025* (2013.01); *G01J 5/20* (2013.01); *G01N 21/3504* (2013.01); *G08B 21/14* (2013.01); *G08B 21/16* (2013.01); *G01N 2201/06186* (2013.01)

(58) Field of Classification Search
USPC ................................................ 356/432–444
See application file for complete search history.

(56) References Cited

U.S. PATENT DOCUMENTS

| | | | |
|---|---|---|---|
| 5,021,663 | A | 6/1991 | Hornbeck |
| 5,912,464 | A | 6/1999 | Vilain et al. |

(Continued)

FOREIGN PATENT DOCUMENTS

| | | |
|---|---|---|
| DE | 10 2004 015 439 A1 | 6/2005 |
| FR | 2 866 115 A1 | 8/2005 |
| WO | WO 95/17014 | 6/1995 |

OTHER PUBLICATIONS

French Preliminary Search Report issued Aug. 27, 2013, in French Application No. 12 62132 filed Dec. 17, 2012 (with English Translation of Categories of Cited Documents).

(Continued)

*Primary Examiner* — Tri T Ton
(74) *Attorney, Agent, or Firm* — Oblon, McClelland, Maier & Neustadt, L.L.P.

(57) ABSTRACT

Infrared detection device comprising a gas detection device comprising a resistive layer, a first portion of which is able to emit infrared radiation able to be absorbed by the gas to be detected, and a second portion of which is thermally coupled to a first element for the thermoresistive transduction of the infrared radiation; a substrate comprising an electronic circuit for controlling and reading the gas detection device; portions of electrically conductive material electrically connecting the first portion and the first thermoresistive transduction element to the electronic circuit, and providing mechanical holding of the first and second portions opposite the substrate so that a distance between the first portion and the substrate is substantially equal to a distance between the second portion and the substrate.

14 Claims, 5 Drawing Sheets

(51) Int. Cl.
  *G01J 5/20* (2006.01)
  *G01J 5/00* (2006.01)
  *G08B 21/14* (2006.01)
  *G08B 21/16* (2006.01)

(56) References Cited

U.S. PATENT DOCUMENTS

| | | | |
|---|---|---|---|
| 6,373,056 B1 | 4/2002 | Johnson et al. | |
| 7,119,337 B1 | 10/2006 | Johnson et al. | |
| 2002/0096492 A1 | 7/2002 | George et al. | |
| 2002/0175284 A1 | 11/2002 | Vilain | |
| 2005/0161605 A1 | 7/2005 | Yokura et al. | |
| 2011/0290986 A1 | 12/2011 | Yon et al. | |

OTHER PUBLICATIONS

U.S. Appl. No. 14/617,042, filed Feb. 9, 2015, Palanchoke, et al.
U.S. Appl. No. 14/107,106, Dec. 16, 2013, Yon, et al.

INFRARED DETECTION DEVICE

TECHNICAL FIELD

This document concerns an infrared detection device advantageously used for fulfilling both a function of detecting elements (persons, objects) or movements in the infrared spectrum, for example to detect the activity of persons, and a gas detection function.

Such a device may in particular be used in the field of automatic control or the management of the comfort of persons in a building.

PRIOR ART

To detect the activity of persons or movements, the use of infrared detection devices of the PIR (Passive Infrared Sensor) type is known. These devices are generally formed from one to four elementary infrared detectors, or pixels, implemented for example using a pyroelectric material, integrated in a hermetic housing, and mounted on an electronic card. The assembly is positioned behind an optical element, for example a sectorised Fresnel lens produced from a plastics material transparent to infrared radiation.

Each sector of the Fresnel lens relates to a particular area of the scene to be monitored, with optionally an overlap between these areas. The infrared pixels are sensitive to the thermal flows emitted by the objects present in their environment. These pixels provide an electrical signal, the characteristics of which depend in particular on the temperature of the object situated opposite the pixels. Thus, when a person moves in the optical field of the PIR device, the thermal flow that this person emits is collected and focused on one or other of the pixels of the PIR device, according to the sector of the Fresnel lens that the person is crossing. In this way, the pixels represent the detected movement of a person by a transition, or modification, of their output signal.

Because the emission of the infrared radiation is mainly independent of the ambient illumination, such an infrared detector functions both in full light and in the most total darkness. This feature is important, in particular for applications for the automatic control of lighting where it may be necessary to detect for example the arrival of a person in a dark room before activating the lighting. The detection of infrared radiation in addition offers a captured image that is almost invariant with the illumination, which generally changes in the course of the day, and therefore makes it possible to use signal processing algorithms that are simpler and therefore more economical in terms of energy and at the same time more robust.

The discrimination abilities of PIR devices do however remain very rudimentary because of their small number of pixels. A PIR device cannot for example distinguish between the presence of a human or a pet, which may be a problem in controlling the switching on of a heating radiator. These confusions lead to false detection alerts, where reducing the number thereof calls for constraining installation recommendations in buildings and/or software learning processes that make the detection equipment complex.

However there are infrared detectors comprising more resolute components where the number of pixels is extended to several hundred, or even a few tens of thousands, arranged in the form of a bidimensional matrix of pixels. This matrix is arranged at the focus of a lens, which projects the infrared scene onto the plane of the detectors, as for example described in the document U.S. Pat. No. 5,021,663.

In order to detect a gas, for example for the purpose of analysing an air quality and/or measuring a content of certain gases in an environment, there also exist infrared devices of the NDIR (Non-Dispersive Infrared) type. These devices exploit the gas absorption properties for certain wavelengths situated in the infrared spectrum. For example, carbon dioxide ($CO_2$) is characterised by two adsorption bands situated respectively at 4.2 µm (a so-called stretching mode) and 15.1 µm (a so-called bending mode). Numerous other gases also have absorption bands in the infrared domain, such as for example carbon monoxide (CO), water vapour ($H_2O$), methane ($CH_4$), CFCs, $N_2O$, etc.

A device of the NDIR type associates an infrared source (which may be broad spectrum), a narrow filter designed to isolate a spectral band corresponding to the gas that it is wished to measure, and an infrared detector intended to detect this spectral band, as for example described in the document U.S. Pat. No. 6,373,056.

Although other devices exist for measuring gas concentrations (electrochemical devices for example), the use of NDIR devices is generally considered to be the best measurement method, in particular because of their ability to detect a wide range of gaseous molecules.

When it is wished to effect both a detection of activity and a detection of gas, it is necessary to use these two types of detector.

DISCLOSURE OF THE INVENTION

Thus there is a need to propose an infrared detection device comprising at least one gas detection device that is technologically compatible with a matrix of infrared detectors in order to be able to integrate the gas detection device and the matrix of infrared detectors in the same element and to implement them via the use of common steps of the same nature.

To this end, one embodiment proposes an infrared detection device comprising at least one gas detection device that comprises at least:
  a resistive layer, at least a first portion of which is able to emit a first infrared radiation in a first range of wavelengths able to be absorbed by the gas or gases to be detected, and at least a second portion of which is thermally coupled to at least one first element for the thermoresistive transduction of the first infrared radiation intended to be detected;
  a substrate comprising at least one first electronic circuit for controlling and reading the gas detection device;
  portions of electrically conductive material electrically connecting at least the first portion of the resistive layer and the first thermoresistive transduction element to the first electronic circuit, and providing mechanical holding of the first portion and second portion of the resistive layer opposite the substrate so that a distance between the first portion of the resistive layer and the substrate is substantially equal to a distance between the second portion of the resistive layer and the substrate.

This embodiment therefore proposes the production of a gas detection device of the infrared type in the form of suspended micro-bridges. The term "suspended micro-bridges" is used here to designate the fact that the portions of the resistive layer are produced above the substrate and maintained at a certain distance from the substrate by the portions of electrically conductive material.

Because the portions of the resistive layer contributing to the emission and detection of the infrared radiation used for the gas detection are arranged, vis-à-vis the substrate, at substantially similar distances, such a device can therefore be produced in the form of an integrated microsystem comprising an infrared source and an infrared sensor produced in the form of suspended micro-bridges and forming a gas detection device of the NDIR type, for example produced via the use of common technological steps.

In such a microsystem, for example intended to be used inside a building for detecting the activity of persons and analysing the air quality, the device can therefore also comprise a matrix of infrared detectors able to produce a bidimensional infrared representation for analysing or detecting movements.

The infrared detectors of the activity detection matrix, the infrared sensor and the infrared emitter or emitters for the gas detection may also all be constructed in the form of suspended micro-bridges, above the same surface of the substrate and maintained at the same distance from this substrate.

The various portions of resistive material of these infrared devices can all be constructed simultaneously, from at least the same resistive layer, according to the same technological method for manufacturing micro-bridges, which both reduces the manufacturing cost and reduces their energy consumption. The integration of these two infrared detection functions within the same device also facilitates communication between the elements fulfilling these two functions.

The first portion of the resistive layer dissipates heat by Joule effect in order to effect the emission of the first infrared radiation. The second portion of the resistive layer couples the free carriers with the infrared radiation received. The resistive layer is for example a metal layer, or a doped semiconductor layer.

The thermal coupling between the second portion of the resistive layer and the first thermoresistive transduction element enables the second portion of the resistive layer to absorb the infrared radiation received and therefore to heat the first thermoresistive transduction element absorbing the heat emitted by the second portion, which modifies the resistivity of this first thermoresistive transduction element. The electrical link, direct or indirect, formed by the portions of electrically conductive material between the first thermoresistive transduction element and the first electronic circuit enables the electronic circuit to measure this change in resistivity.

The first portion and the second portion of the resistive layer may be isolated electrically from each other when the functions of emission and detection of the first infrared radiation are performed by two separate elements of the gas detection device. The first portion of the resistive layer therefore forms part of an infrared emitter of the gas detection device, and the second portion of the resistive layer coupled to the first thermoresistive transduction element forms part of an infrared sensor of the gas detection device.

The device may also comprise a matrix of infrared detectors such that each infrared detector comprises at least:
  a third portion of the resistive layer coupled thermally to at least a second element for the thermoresistive transduction of a second infrared radiation in a second range of wavelengths intended to be detected;
  portions of electrically conductive material electrically connecting the second thermoresistive transduction element to a second electronic circuit controlling and reading the matrix of infrared detectors implemented in the substrate, and providing mechanical holding of the third portion of the resistive element opposite the substrate such that a distance between the third portion of the resistive layer and the substrate is substantially equal to the distance between the second portion of the resistive layer and the substrate.

The third portion of the resistive layer may be electrically isolated from the first and second portions of the resistive layer.

Such a device, for example used in the field of building automation, therefore comprises two types of infrared detection elements, one used for a gas detection and the other used for a detection of persons or activity, integrated in the same device. Equipping rooms in a building with two separate types of sensor is thus avoided, which reduces the installation cost thereof and facilitates communication between them.

The first and second electronic circuits may be a single device, for example produced in the form of a single integrated circuit, which may comprise several functional units dedicated to the control and processing of signals issuing from the emitting and receiving elements of the gas detection device and the matrix of infrared detectors.

Each infrared detector may also comprise at least one portion of reflective metal material arranged between the substrate and the third portion of the resistive layer of the infrared detector, the distance between the third portion of the resistive layer and the portion of reflective metal material, in each of the infrared detectors, being equal to approximately one quarter of the wavelength belonging to the second range of wavelengths and intended to be detected by the infrared detector. In this way, in the infrared detectors, cavities of the "quarter wave" type are produced, which afford good electromagnetic impedance matching (relating to the electromagnetic wave coupling with the resistive layer) of both the gas detection device and the matrix of infrared detectors while having the portions of resistive material of the gas detection device and of the matrix of infrared detectors arranged at the same distance from the substrate. The matrix of infrared detectors may be a matrix of microbolometers.

Each of the third portions of the resistive layer may have electromagnetic impedance substantially equal to twice an electromagnetic impedance of the second portion of the resistive layer.

The matrix of infrared detector may be coupled optically to an optical focusing system.

The device may also comprise at least one portion of material the resistivity of which is greater than that of the material of the resistive layer, arranged on the first portion of the resistive layer so that the first infrared radiation is intended to be emitted through said portion of material. This portion of material may issue from a layer, other portions of which form the first and/or second thermoresistive transducer element, and is for example a semiconductor such as amorphous silicon.

The first thermoresistive transduction element may comprise a first portion of amorphous silicon and/or, when the device comprises the matrix of infrared detectors, the second thermoresistive transduction element may comprise a second portion of amorphous silicon and/or, when the device comprises the portion of material the resistivity of which is greater than that of the material of the resistive layer, said portion of material may comprise amorphous silicon.

Said portion of material the resistivity of which is greater than that of the material of the resistive layer may comprise amorphous silicon.

At least one of the first thermoresistive transduction element and the second thermoresistive transduction element may comprise a first or a second portion of amorphous silicon.

The device may further comprise a housing in which the gas detection device and/or the matrix of infrared detectors is or are hermetically enclosed, the housing comprising at least a first portion of material transparent vis-à-vis the first range of wavelengths arranged opposite the gas detection device and/or at least a second portion of material transparent vis-à-vis the second range of wavelengths arranged opposite the matrix of infrared detectors.

The device may further comprise:
a first optical filter coupled to the first portion of material transparent vis-à-vis the first range of wavelengths and able to effect an optical filtering such that only the wavelengths intended to be absorbed by the gas or gases to be detected can pass through the first optical filter; and/or
a second optical filter coupled to the second portion of material transparent vis-à-vis the second range of wavelengths and able to effect an optical filtering such that only the wavelengths of the second range of wavelengths can pass through the second optical filter.

The resistive layer may comprise TiN and/or $MoSi_2$ and/or $WSi_2$.

The device may further comprise an optical reflection device arranged in an enclosure, or chamber, intended to contain the gas or gases to be detected and able to reflect the first infrared radiation emitted by the first portion of the resistive layer towards the second portion of the resistive layer.

The resistive layer may be such that the ratio of the resistivity of the material of the resistive layer to the thickness of the resistive layer is equal to approximately 188 Ohms.

It is also proposed a method for producing an infrared detection device, comprising at least the production of a gas detection device obtained by implementing the steps of:
producing, in a substrate, at least one first electronic circuit for controlling and reading the gas detection device;
depositing at least one layer of sacrificial material on the substrate;
depositing at least one resistive layer on the layer of sacrificial material;
etching the resistive layer and the layer of sacrificial material, forming at least one first portion of the resistive layer able to emit a first infrared radiation in a first range of wavelengths able to be absorbed by the gas or gases to detected, and at least one second portion of the resistive layer;
producing at least a first element for thermoresistive transduction of said first infrared radiation intended to be detected, the first thermoresistive transduction element being thermally coupled to the second portion of the resistive layer;
producing portions of electrically conductive material electrically connecting at least the first portion of the resistive layer and the first thermoresistive transduction element to the first electronic circuit;
eliminating the layer of sacrificial material, the portions of electrically conductive material providing a mechanical holding of the first portion and second portion of the resistive layer opposite the substrate such that a distance between the first portion of the resistive layer and the substrate is substantially equal to a distance between the second portion of the resistive layer and the substrate.

The method may further comprise the production a matrix of infrared detectors obtained by implementing the steps of:
etching the resistive layer so that it also forms a plurality of third portions of the resistive layer;
producing a plurality of second elements for the thermoresistive transduction of a second infrared radiation in a second range of wavelengths intended to be detected, each of the second thermoresistive transduction elements being thermally coupled to one of the third portions of the resistive layer;
producing portions of electrically conductive material electrically connecting the second thermoresistive transduction elements to a second electronic circuit for controlling and reading the matrix of infrared detectors produced in the substrate, and providing mechanical holding of the third portions of the resistive layer opposite the substrate such that a distance between each of the third portions of the resistive layer and the substrate is substantially equal to the distance between the second portion of the resistive layer and the substrate.

The method may further comprise, before the deposition of the layer of sacrificial material on the substrate, the production, on the substrate, of portions of reflective metal material such that each portion of reflective metal material is arranged between the substrate and one of the third portions of the resistive layer, the distance between said one of the third portions of the resistive layer and said portion of reflective metal material being able to be equal to approximately one quarter of a wavelength belonging to the second range of wavelengths and intended to be detected by the matrix of infrared detectors. In this way, in the infrared detectors, quarter-wave cavities are produced that make it possible to have a good electromagnetic impedance matching, affording good absorption of the electromagnetic radiation.

BRIEF DESCRIPTION OF THE DRAWINGS

The present invention will be better understood from a reading of the description of example embodiments given purely by way of indication and in no way limitatively, referring to the accompanying drawings in which.

Identical, similar or equivalent parts of the various figures described below bear the same numerical references so as to facilitate passing from one figure to another.

The various parts shown in the figures are not necessarily shown to a uniform scale, in order to make the figures more legible.

The various possibilities (variants and embodiments) must be understood as not being exclusive of one another and may be combined with one another.

DETAILED DISCLOSURE OF PARTICULAR EMBODIMENTS

Figure 1:
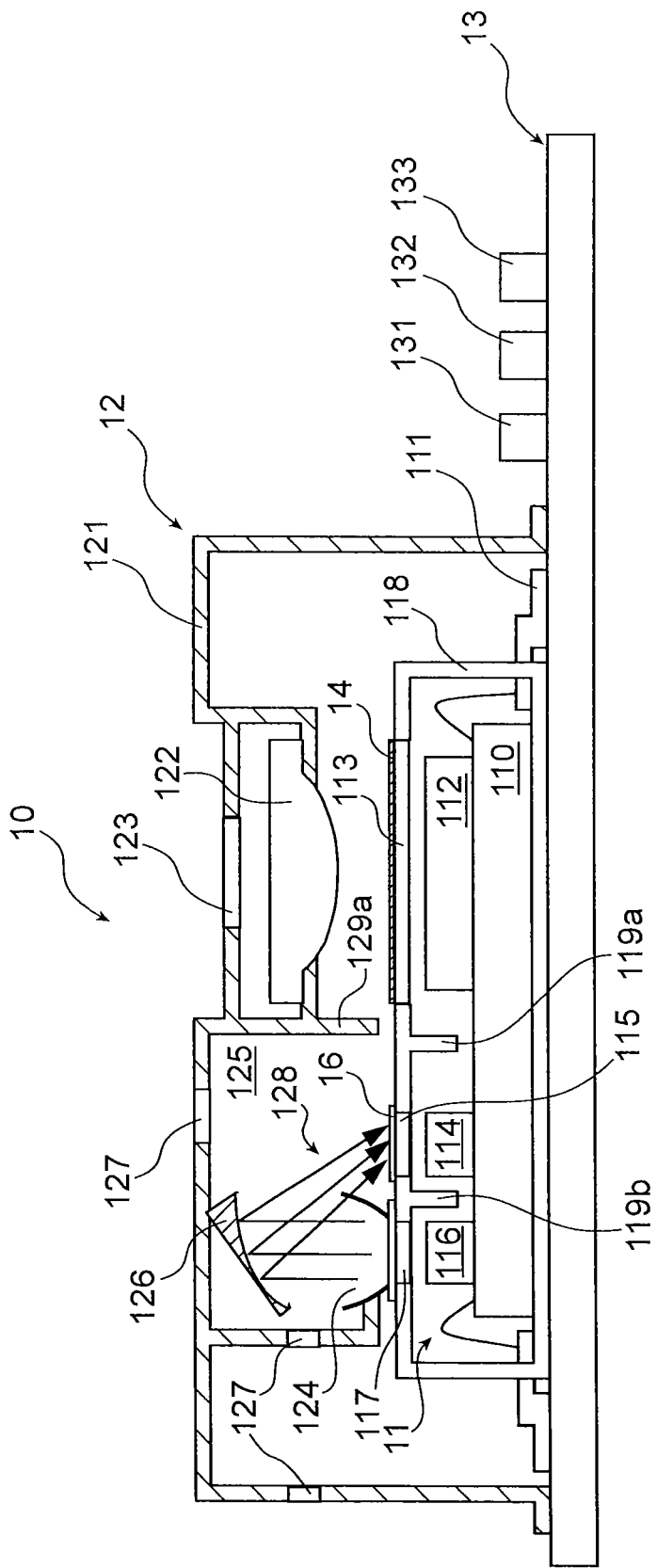
FIG. 1 shows an infrared detection device according to a particular embodiment.

FIG. 1 shows an example embodiment of an infrared detection device 10, produced in the form of a microsystem, the various electronic elements of which forming a gas detection device 11 and a matrix of infrared detectors 112 are enclosed in an optical housing 12 arranged on a support, which is here an electronic card 13.

The device 10 comprises an electronic control and reading circuit 110 produced in the form of an integrated circuit, for example in CMOS technology. The gas detection device 11 comprises an infrared sensor 114 able to effect an infrared detection in a first range of wavelengths of the infrared domain and an infrared emitter 116 forming an infrared emitting source, the emission spectrum of which corresponds at least partly to the detection domain of the infrared sensor 114. The infrared sensor 114 and the infrared emitter 116 are integrated on the electronic circuit 110, which carries out the control and reading of the infrared sensor 114 and of the infrared emitter 116.

The matrix of infrared detectors 112, forming a matrix of infrared pixels able to effect detection in a second range of wavelengths of the infrared domain, is also integrated on the electronic circuit 110, which also carries out the control and reading of the infrared detectors of the matrix 112. The matrix 112 is for example a square matrix where the number of pixels, that is to say the number of infrared detectors, per row and per column, is between approximately 30 and 100. Larger formats may be provided, in particular when the observation field so requires (a large hall for example). The elements 110, 112, 114 and 116 are mounted in a housing 118 that has various windows 113, 115, 117 opposite respectively elements 112, 114, 116 and transparent to the respective emission of reception wavelengths of these elements. The housing 118 is hermetically closed in order to protect the devices 110, 112, 114 and 116 from the external environment.

The window 113, which is arranged opposite the matrix of infrared detectors 112, is produced from a material transparent to the second range of wavelengths, for example made from germanium or silicon, and advantageously has an optical filter 14, produced for example in the form of a Bragg filter, which makes it possible to select the second range of wavelengths, preferentially corresponding to the domain of the infrared spectrum lying between approximately 8 µm and 15 µm, this range comprising the wavelengths corresponding to the spectral signature of the objects at ambient temperature transmitted in the atmosphere. This spectral range is therefore particularly well suited to the detection of the activity of persons intended to be carried out by the matrix of infrared detectors 112.

As an alternative to the Bragg filter, the optical filter 14 may be a non-reflective layer, more simple in design than a Bragg filter, in particular for applications where the field of observation does not include an intense infrared source (such as for example the sun), for example inside buildings. The optical treatment of the window 113, that is to say the Bragg filter or the non-reflective layer, may advantageously be carried out on both faces of the window 113, that is to say inside and outside the housing 118. On each of the two main faces of the window 113, it is therefore possible to produce a Bragg filter or a non-reflective layer (either a Bragg filter on each side of the window 113, or a non-reflective layer on each side of the window 13, or a Bragg filter on one side and a non-reflective layer on the other).

The function of the window 115 that is arranged opposite the infrared sensor 114 is to filter and transmit to the infrared sensor 114 the wavelengths of the first range of infrared wavelengths used to measure the concentration or concentrations of gas required. It may be produced from a material transparent to infrared such as silicon, germanium, zinc sulphide, zinc selenide, etc, which are materials suitable for covering an extensive infrared spectrum (that is to say a spectrum comprising a lower limit for example of between approximately 0.55 µm and 1.8 µm, and an upper limit for example of between approximately 12 µm and 23 µm, for example approximately 15 µm).

The material of the window 115 is chosen so as to be transparent to at least the first range of wavelengths. If the gas detection function relates to an absorption peak situated in a more restricted range of wavelengths (the case for example of the detection of $CO_2$ at approximately 4.26 µm, or CO at approximately 4.61 µm), the choice of the material of the window 115 may be extended to other materials such as aluminium oxide ($Al_2O_3$, transparent for wavelengths of less than or equal to approximately 5.5 µm), magnesium fluoride ($MgF_2$, transparent for a wavelength of less than or equal to approximately 7.5 µm) or to polymers transparent to infrared (HDPE, high-density polyethylene), these alternative materials being favoured for example for reasons of cost, strength or ease of manufacture and/or integration. Advantageously, the window 115 also has a narrow bandpass filter 16 centred on the absorption band or bands of the gas or gases intended to be detected by the infrared sensor 114.

The width halfway up the filter is generally around 0.1 µm so as to discriminate the gas or gases sought from the other molecules that would have an adjacent absorption band. It may be produced for example in the form of a Bragg filter and/or in the form of a nanostructured filter, and this on one side and/or the other of the window 115, that is to say inside and/or outside the housing 118.

The function of the window 117 that is arranged opposite the infrared emitter 116 is to transmit the infrared flow emitted by the infrared emitter 116, and more particularly at least the part of the radiation emitted by the infrared emitter 116 the wavelengths of which correspond to the absorption band or bands of the gas or gases to be detected. The same materials as those already described for the window 115 may be used. A non-reflective layer (visible but not referenced in FIG. 1) deposited against the window 117, inside or outside the housing 118, may be advantageous for limiting the Fresnel reflections and thus maximising the intensity of the infrared radiation emitted by the infrared emitter 116. It is also possible to have a non-reflective layer at the two main faces of the window 117, inside and outside the housing 118.

In a variant, the windows 113, 115 and 117 may be produced in the form of a single window arranged opposite the three elements 112, 114 and 116 and produced from a material transparent to the first range of infrared wavelengths (intended to emitted by the infrared emitter 116 and detected by the infrared sensor 114) and to the second range of infrared wavelengths (intended to be detected by the matrix of infrared detectors 112). In this case, the optical treatments (filters, non-reflective layers, etc) particular to the first and second ranges of wavelength may be carried out locally on areas of the windows situated opposite the elements 112, 114 and 116 that correspond thereto.

In the examples described above, the first range of wavelengths belongs to the band of medium infrared wavelengths (referred to as MWIR and lying between approximately 3 µm and 8 µm) and the second range of wavelengths belongs to the band of long infrared wavelengths (referred to as LWIR and lying between 8 µm and 15 µm). It is also possible for the first and/or second wavelengths to belong to the band of short infrared wavelengths (referred to as SWIR and lying between approximately 1.4 µm and 3 µm).

In another variant, the first and second ranges of wavelengths may be adjacent to each other and/or belong to the same band of infrared wavelengths, that is to say long or medium or short as previously described. The wavelengths belonging to one of these three bands of infrared wavelengths have similarities in terms of optical properties. In this case, the production of the windows 113, 115 and 117 may then be simplified using first the same material for producing these windows and secondly the same manufacturing methods for effecting the optical treatments (filters), at least for the windows 113 and 117.

According to a variant embodiment, the infrared sensor 114 and the infrared emitter 116 may be produced in the form of a single device, for example a bolometer or microbolometer, the equilibrium temperature of which results from the global energy balance of the system determined at least partly by the infrared energy absorbed by the gas or gases to be detected.

According to a variant embodiment, the gas detection device 11 may comprise several infrared sensors 114 and thus detect and measure independently several different gases. Each of the infrared sensors 114 may then be associated with a window 115 distinct from the windows associated with the other infrared sensor 114, thus each having a filter the pass-band of which is suited to the gas to be detected by said infrared sensor. In this variant, the gas detection device 11 may comprise a single infrared emitter 116 if its emission spectrum is sufficiently wide to cover all the absorption bands of the gases to be detected, such as for example when the infrared emitter 116 is of the black body type and is for example an incandescent filament or a resistive thin film, and if the absorption bands of the various gases are situated in the same infrared band, MWIR for example. It is also possible for the gas detection device 11 to comprise several infrared emitters 116 in order to cover all the absorption bands of the gases to be detected.

Advantageously, at least some of the elements 112, 114 and 116 may function under reduced atmospheric pressure, in particular when these elements are produced from thermal components (for example in the case of infrared emitters 116 produced in the form of one or more resistive thin films, and a matrix of infrared detectors 112 and/or an infrared sensor 114 of the pyroelectric, thermoelectric or microbolometer type). Such a reduced atmospheric pressure may be obtained at the time of the hermetic closure of the housing 118, by performing this operation under vacuum according to methods such as for example pinching a pip or a by assembling the body and cap of the housing 118 under vacuum by re-melting a weld preform. Another means of obtaining functioning of the elements 112, 114 and 116 under vacuum is to provide integration thereof in one or more hermetic cavities arranged directly on the electronic circuit 110, which makes it possible to maintain a low pressure around the thermal components of the elements 112, 114 and 116. Examples of such hermetic cavities integrated directly on a circuit are for example described in the documents US 2002/0175284 A1 and WO 95/17014. The cavities under low pressure may thus be obtained by depositing thin layers on a layer of sacrificial material structured by surface micro-machining. These cavities under low pressure may also be obtained by sealing two substrates according to various possible methods such as anodic sealing, welding by thermocompression or re-melting of a metal bead. The elements (thin films or substrates) used to close the cavities may serve as a support for positioning the filters and/or the non-reflective treatment of the windows 113, 115 and 117.

In the infrared detection device 10, a single technology is used to manufacture both the gas detection device 11, that is to say the infrared emitter or emitters 116 and the infrared sensor or sensors 114, and the matrix of infrared detectors 112.

In addition, apart from the normal functions of controlling and reading the elements 112, 114 and 116, the electronic circuit 110 is also designed to supervise the information issuing from these various elements and to process the interactions between the activity detection and gas detection functions. This supervision ability can be used for example to satisfy automation requirements by facilitating a reliable decision making by virtue of the merging of the information delivered by the matrix of infrared detectors 112 and by the infrared sensor 114. The possibility of controlling two types of detector in a centralised manner and processing the supplementary information may also be used to save on the energy consumed by the infrared detection device 10, which will be able proceed with targeted requests, either of detection of activity or gas detection, depending on the application scenario envisaged and according to the context of the moment.

Electrical connections 111 of the housing 118 are electrically connected to the electronic card 13 and to the inputs and outputs of the electronic circuit 110, for example by wired welds. The electronic card 13 also comprises additional electronic components 131, produced in the form of discrete components and integrated circuits, used to control the electronic circuit 110 (supply unit, clock, etc) and/or to process and transmit the signals delivered by the electronic circuit 110 (alarm, command control, RF connection, internet, etc) to an external device, for example a system for ventilation, lighting, heating, etc. Advantageously, the electronic card 13 also comprises a visible light detector 132, for example produced in the form of a silicon photodiode and used as a sensor for the automatic control of the lighting in addition to the function of detection of persons fulfilled by the matrix of infrared detectors 112. It is also advantageous to provide on the electronic card 13 a temperature sensor 133, for example produced in the form of an integrated circuit, used as a sensor for the temperature of the air, in addition to the information on the temperature of objects (the wall of a room for example) that can be measured by the matrix of infrared detectors 112.

In the example in FIG. 1, the electronic card 13 also supports an optical housing 12, comprising here two parts. A first part, located substantially above the matrix of infrared detectors 112 and the window 113, supports an optical focusing system the function of which is to project the image of a scene onto a focal plane merged with the plane of the matrix of infrared detectors 112, through the window 113. The optical focusing system comprises for example a convergent lens 122 associated with a diaphragm 123 open in a body 121 of the optical housing 12. A second part of the optical housing 12, located substantially above the infrared sensor 114 and the infrared emitter 116, forms a chamber 125 for analysing a gaseous mixture.

In this analysis chamber 125, a ray concentrator 124 is arranged above the window 117 and opposite a mirror 126 also arranged in the analysis chamber 125. The association of the infrared emitter 116, the window 117, the concentrator 124, the analysis chamber 125, the mirror 126 and the infrared sensor 114 associated with a narrow interferential filter 16 located on the window 115 forms an NDIR device able to analyse the concentration of at least one species of a gaseous mixture that is introduced into the analysis chamber 125 through openings 127 formed through the body 121 of the housing 12. The openings 127 enable the gaseous mixture situated in the chamber 125 to be renewed by diffusion of chemical species. A pump system, for example activated periodically, may optionally be provided to accelerate the renewal of the species in the analysis chamber 125, at the cost however of an electrical consumption and cost greater than the infrared detection device 10.

The function of the concentrator 124 is to produce, using the infrared emitter 116, an infrared beam 128 collimated in the direction of the mirror 126, which then reflects it in the direction of the infrared sensor 114. The optical path of the infrared beam 128 between the windows 117 and 115, through the gaseous mixture, gives rise to infrared absorption phenomena that are dependent on the nature of the gaseous mixture present in the analysis chamber 125. Measurement of the infrared flow received by the infrared sensor 114 after attenuation through the gas or gases to be detected makes it possible to estimate the concentration of at least one constituent of the mixture, the absorption peak of which corresponds to the pass-band of the filter of the window 115. Other design options, for example multiple reflexion architectures, may be provided to increase the length of the optical path and improve the resolution of the analysis. It is also possible to provide a reference optical channel comprising for example a hermetic analysis chamber loaded with a reference gas or a secondary analysis chamber, in communication with the main analysis chamber, characterised by a substantially different optical path length.

Another alternative is to provide a reference optical channel using an optical fibre situated outside the absorption bands of the gases that the system is liable to encounter.

Advantageously, the infrared detection device 10 may comprise an optical screen 119*b* arranged between the infrared emitter 116 and the infrared sensor 114 and isolating the infrared sensor 114 from the direct illumination of the infrared emitter 116 (that is to say without passing through the analysis chamber 125). Likewise, the optical isolation between the part of the infrared detection device 10 responsible the detection of activity and the one responsible for the detection of gases may be improved by optical screens 119*a* and 129*a* formed between the elements intended to fulfil these two functions.

These optical screens are for example produced in the form of faces internal to the housing 118 and to the optical housing 12. They are optionally attached or provided at the time of machining (or moulding) said housings.

The infrared detection device 10 may also provide the integration of an additional infrared source used to calibrate the infrared detectors of the matrix 112. Such a calibration of the infrared detectors of the matrix 112 is advantageous since it makes it possible to refer back to the apparent temperature of the objects present in a scene (the apparent temperature of the walls, for example, which contributes to the comfort felt by the occupants). According to this arrangement, an infrared source emits a calibrated infrared flow, through a frosted window arranged on the housing 118, in the direction of a mirror supported by the optical housing 12, which returns a diffuse image of the source, projected uniformly onto the surface of the matrix of infrared detectors 112. The matrix of infrared detectors 112 can therefore be illuminated by two separate methods: by the scene through the focusing lens 122 and by the calibrated source. An electromechanical system (for example an electromagnet actuating a movable mirror) may be provided to select one or other of the two methods.

An example of a method for producing the infrared emitter 116, the infrared sensor 114 and the matrix of infrared detectors 112 is now described in relation to FIGS. 2*a* to 2*f*. These three elements are integrated on a single substrate 109 and use the same manufacturing technology. The unicity of technology for producing these three elements makes it possible first to produce them simultaneously and secondly to duplicate them a large number of times on the substrate 109 by means of the collective techniques of micro-manufacture in the field of semiconductors.

Each of FIGS. 2*a*-2*f* shows a view in profile cross section of the infrared emitter 116, the infrared sensor 114 intended to detect at least an absorbent gas for example in the MWIR range (typically $CO_2$ with a wavelength of approximately 4.26 µm), and an infrared detector forming a pixel of the matrix of infrared detectors 112 intended to detect an activity and functioning for example in the LWIR infrared range lying between approximately 8 µm and 15 µm, produced via the implementation of steps of depositing thin layers, photolithography, etching of thin layers by dry or wet method, cleaning of resins and etching residues, mecano-chemical polishing, etc.

Figure 2A:
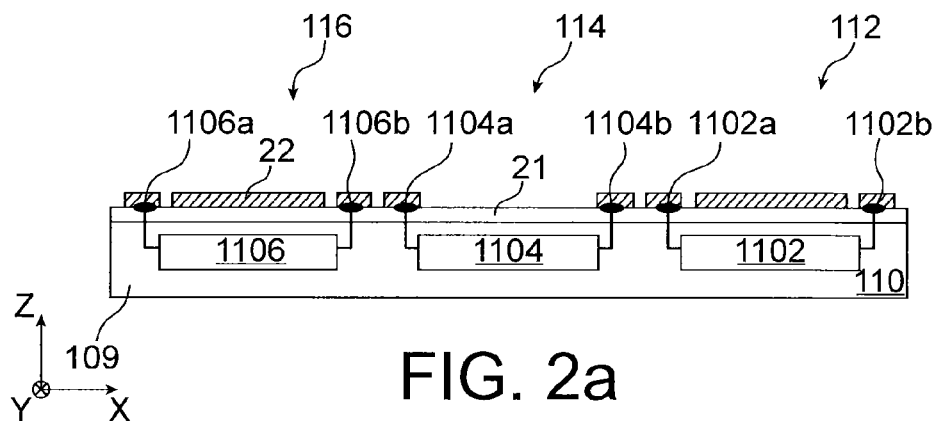
FIGS. 2a to 2f and 4 show steps of a method for producing an infrared detection device according to a particular embodiment.

FIG. 2*a* shows the substrate 109, for example composed of silicon, on which there is integrated the electronic circuit 110, which comprises three functional units 1102, 1104, 1106, respectively designed to control and process the signals delivered by the matrix of infrared detectors 112 and by the infrared sensor 114, and to control the infrared emitter 116. Electrical connection pads 1102*a*, 1102*b*, 1104*a*, 1104*b*, 1106*a*, 1106*b* are provided on the surface of the substrate 109 and are intended to provide electrical connections between the functional units 1102, 1104 and 1106 and the corresponding infrared elements 112, 114, 116. These electrical connection pads 1102*a*, 1102*b*, 1104*a*, 1104*b*, 1106*a*, 1106*b* are produced through a passivation layer 21, for example comprising a dielectric material such as silicon oxide or silicon oxynitride, produced on the substrate 109, the function of which is to isolate and protect the active elements of the electronic circuit 110.

A layer of reflective metal material 22, for example formed from a stack of a layer of titanium and a layer of aluminium, is deposited on the passivation layer 21 and then structured by photolithography and etching so as to preserve one or more portions of reflective metal material 22 under each of the infrared detectors of the matrix of infrared detectors 112. One or more other portions of reflective metal material 22 will also preferentially be preserved at the electrical connection pads 1102*a*, 1102*b*, 1104*a*, 1104*b*, 1106*a* and 1106*b* in order to improve the electrical contact between the electronic circuit 110 and the infrared circuits 112, 114 and 116, which will be electrically connected to these electrical connection pads. At least a portion of the reflective metal material 22 may also be preserved at the infrared emitter 116, as shown in FIGS. 2*a*-2*f*. On the other hand, the reflective metal material 22 is eliminated at the infrared sensor 114 for reasons of electromagnetic impedance matching described below.

Figure 2B:
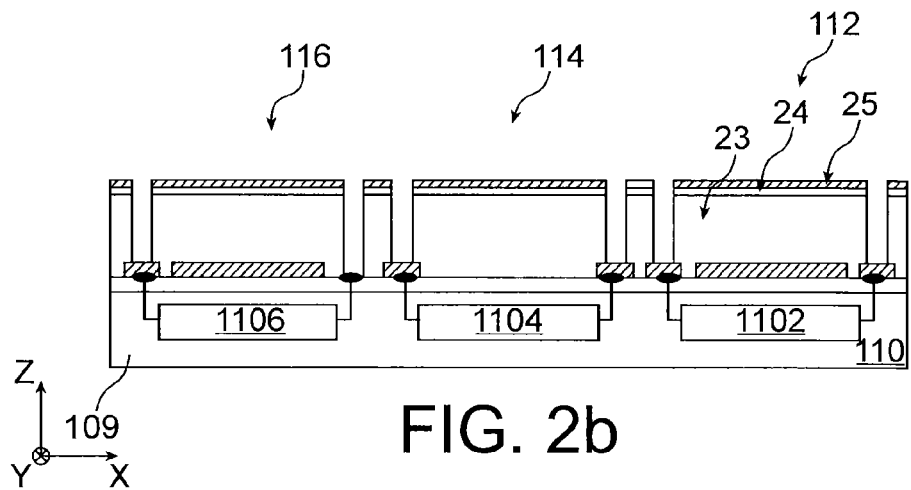

As shown in FIG. 2*b*, deposition and planarization are carried out of a layer of sacrificial material 23, for example comprising polyimide, on the passivation layer 21 and on the remaining portions of the reflective metal material 22. A first dielectric layer 24, for example comprising silicon oxide or silicon nitride, is next deposited on the layer of sacrificial material 23, and then a resistive layer 25, here metal, is deposited on the first dielectric layer 24. The resistive layer 25 is such that the values of the resistivity of the material used and its thickness are adapted to optimise the absorption of the infrared radiation intended to be received by the infrared sensor 114 and by the matrix of infrared detectors 112. Thus the resistive layer 25 is produced such that it has particular electrical characteristics leading to a partial optical absorption of the infrared radiation (approximately 50% in the absence of a cavity, which may be increased up to 100% for a chosen wavelength when a cavity is present, as described below). The resistive layer 25 therefore corresponds to a semi-absorbent layer. The resistive layer 25 may comprise titanium nitride (TiN), or other materials such as molybdenum silicide ($MoSi_2$) or tungsten silicide ($WSi_2$). The thickness of the layer of sacrificial material 23 is for example approximately 2.5 µm, and is chosen according to a required distance between the substrate 109 and the resistive layer 25. The material of the sacrificial layer 23 is chosen so that it can be etched selectively with respect to the materials present (passivation layer 21, reflective metal material 22, material of the first dielectric layer 24, etc).

The three layers 23, 24 and 25 are etched locally in line with or opposite the electrical connection pads 1102a, 1102b, 1104a, 1104b, 1106a, 1106b, optionally using the resistive layer 25 as a hard mask, or any other material able to serve as a hard mask and which would then be removed, thus forming holes and/or trenches for accessing the portions of reflective metal material 22 covering the electrical connection pads 1102a, 1102b, 1104a, 1104b, 1106a, 1106b.

Figure 2C:
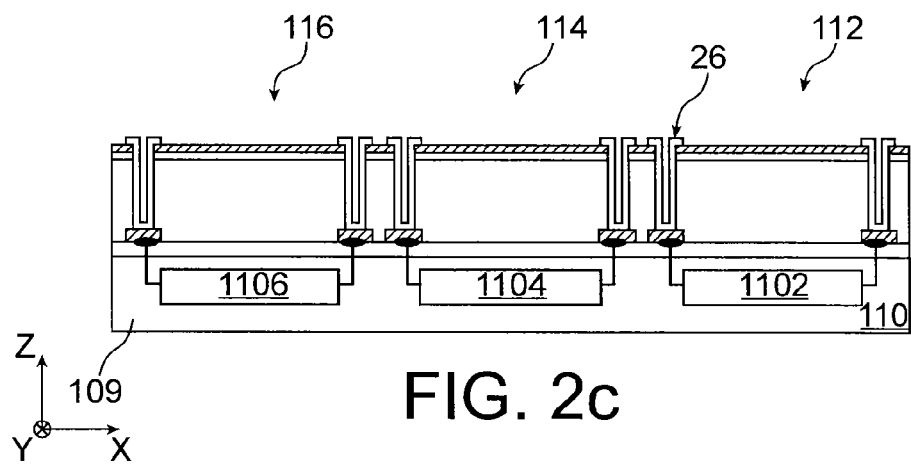

A deposition is then carried out of at least one layer of electrically conductive material, for example metallic, on the resistive layer 25 and in the holes and/or trenches forming the accesses to the electrical connection pads 1102a, 1102b, 1104a, 1104b, 1106a, 1106b through the layers 23, 24 and 25 in order to provide the electrical and mechanical continuity between the electrical connection pads 1102a, 1102b, 1104a, 1104b, 1106a, 1106b (via the portions of reflective metal material 22 covering these pads) and the portions of the resistive layer 25 of each of the infrared elements 112, 114 and 116 (FIG. 2c). This layer comprises for example aluminium and/or titanium and/or tungsten silicide (WSi). The layer is next defined (for example by photolithography) and etched so as to limit the extent thereof on the resistive layer 25 solely to the surface area necessary for a good take-up of electrical contact with the portions of the resistive layer 25. The remaining portions of this layer form portions of electrically conductive material 26 intended to electrically connect the portions of the resistive layer 25 to the electronic circuit 110 and to ensure mechanical holding of these portions (and other materials) when the layer of sacrificial material 23 is etched subsequently.

Figure 2D:
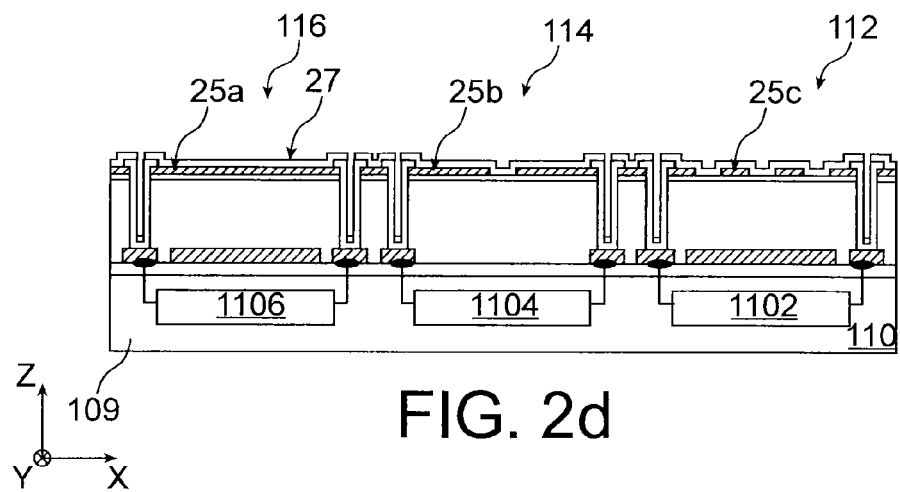

As shown in FIG. 2d, next areas or portions of metal are defined, intended to effect an emission or reception of infrared rays, for the infrared emitter 116, the infrared sensor 114 and the matrix of infrared detectors 112, by photolithography and etching of the resistive layer 25 according to a configuration, or pattern, suited to the electrical characteristics and the infrared absorption or emission characteristics required for the three infrared devices 116, 114 and 112. This etching thus forms at least:

- a first portion 25a of the resistive layer 25, forming part of the infrared emitter 116 and intended to effect an emission of a first infrared radiation in the first range of wavelengths able to be absorbed by the gas or gases to be detected by the gas detection device 11;
- a second portion 25b of the resistive layer 25, forming part of the infrared sensor 114 and intended to cooperate with the detection of the first infrared radiation after absorption by the gas or gases to be detected by the gas detection device 11;
- for each infrared detector of the matrix of infrared detectors 112, at least a third portion 25c of the resistive layer 25, intended to cooperate with the detection of a second infrared radiation in the second range of wavelengths intended to be detected by the matrix of infrared detectors 112.

The material of the resistive layer 25 is such that a portion (here the portion 25a) of this layer is able to produce an infrared radiation when this portion has an electric current pass through it, and so that a portion (the portions 25b and 25) of this layer is able to produce heat when it receives an infrared radiation.

The pattern of the portions 25a, 25b and 25c, that is to say the geometry of these portions in the plane (X;Y), will in particular depend on the ranges of wavelengths intended to be emitted and received by the elements 112, 114 and 116, the required electromagnetic impedance of these portions, the electrical resistance thereof, etc. Examples of patterns of these portions 25a, 25b and 25c are detailed below.

The deposition is next carried out of a second dielectric layer 27, for example comprising silicon oxide or silicon nitride, on the remaining portions 25a, 25b, 25c of the resistive layer 25, on the first dielectric layer 24 (where the resistive layer 25 is etched) and on the portions of electrically conductive material 26.

Advantageously, at least one of the dielectric layers 24 and 27 may be produced so that it absorbs sufficient infrared radiation in the first and/or second range of wavelengths, for example here both in the LWIR band and in the MWIR band. For this, at least one of these two dielectric layers 24 and 27 may comprise silicon nitride ($Si_3N_4$), which has numerous absorption bands in the infrared range.

The absorption is also reinforced if at least one of these layers 24 and 27 has a thickness of at least approximately 400 nm.

Figure 2E:
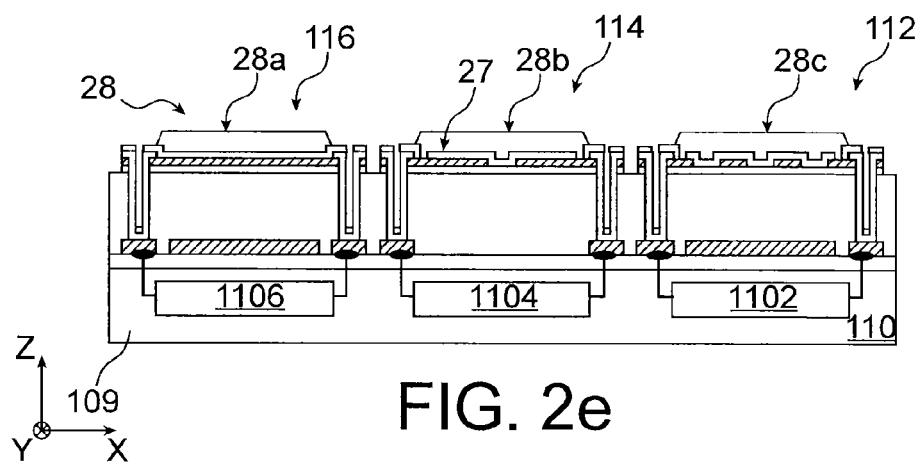

During the following step shown in FIG. 2e, openings are defined through the second dielectric layer 27, forming electrical accesses to the portions 25b and 25c of the resistive layer 25. The deposition is then carried out of a layer 28 comprising a material sensitive to temperature, that is to say the electrical conductivity of which varies according to the temperature thereof, for example where the electrical conductivity increases exponentially with temperature. This layer 28 comprises for example amorphous silicon, polycrystalline silicon, amorphous or polycrystalline germanium, or metal oxides such as for example vanadium oxide. The layer 28 may be a low-doping semiconductor layer making it possible to obtain a good thermoresistive transduction, comparable to a dielectric. The layer 28 is then structured by lithography and etching so that remaining portions of this layer 28 occupy solely the central areas of the elements 112, 114 and 116, and so that peripheral areas (in particular at the portions of electrically conductive material 26 and in the near environment thereof) are left clear in order to improve the thermal insulation between the infrared elements 112, 114 and 116 and the thermal insulation with the substrate 109. In the example in FIG. 2e, remaining portions 28a, 28b and 28c of the layer 28 are present respectively on the portions 25a, 25b and 25c of the resistive layer 25. Because of the openings previously produced through the second dielectric layer 27, the portion 28b is thermally coupled to the portion 25b of the resistive layer 25. This portion 28b has its electrical resistance intended to vary according to the variation in temperature of the portion 25b caused by the infrared radiation detected by the infrared sensor 114. This variation in the electrical resistance of the portion 28b can be detected because this portion 28b is electrically connected to the circuit 110 by the portions of electrically conductive material 26, here via the portion 25b of the resistive layer 25. The portion 28c is thermally coupled to the portion 25c of the resistive layer 25. Here the portion 28c is also electrically coupled, through the openings previously formed in the second dielectric layer 27, to the portion 25c, which forms the electrical connection between the portion 28c and the circuit 110 via the portions of electrically conductive material 26. This portion 28c has its electrical resistance, which is intended to vary according to the variation in temperature of the portion 25c, linked to the infrared radiation detected by the associated infrared detector. The portions 28b and 28c of the temperature-sensitive material are intended to form a thermoresistive transducer respectively of the infrared sensor 114 and of the infrared detector of the matrix 112, the portions of the resistive layer 25 providing the absorption of the infrared radiation received. In the example in FIG. 2e, a portion 28a of the layer 28 is also preserved above the portion 25a of the resistive layer 25 of the infrared emitter 116. The portions of the layer 28 are able to have the infrared radiation emitted and received by the elements 112, 114 and 116 pass through them.

A last photolithographic level is defined in order to electrically and thermally isolate the devices 112, 114, 116 from one another by etching of the layers 27, 25, 24 and optionally 28. This etching also defines, in the layers 24, 25 and 27, portions with a reduced cross section 30 (visible in FIGS. 3a to 3c described below), in line with said devices so as to electrically connect the portions 25a, 25b and 25c to the portions of electrically conductive material 26. A reduced cross section, corresponding for example to a width of between approximately 0.3 μm and 10 μm, for a thickness for example of between approximately 20 nm and 2 μm depending on the nature of the layers 27 and 24, is preferably produced in order to improve the thermal insulation of said devices.

These portions 30 form thermal insulation arms the length of which is for example between approximately 2 μm and 90 μm when it is a case of portions 30 in the form of beams.

Figure 2F:
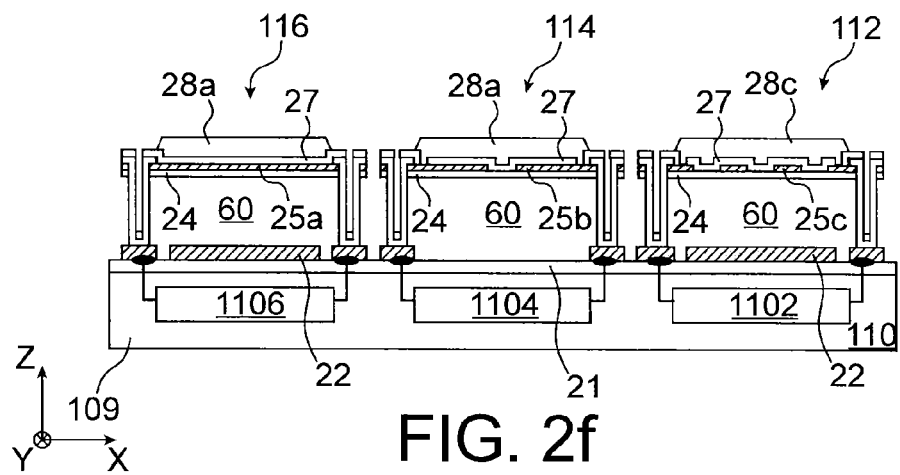

As shown in FIG. 2f, the layer of sacrificial material 23 is eliminated, for example by chemical etching in oxygen plasma when the layer of sacrificial material 23 comprises polyimide. In this way the three infrared devices 112, 114 and 116 are obtained, produced in the form of suspended micro-bridges, integrated on the same substrate, but each produced so that its electrical and electro-optical properties are adapted to a particular infrared emission or detection function. The suspended micro-bridge architecture of the three devices 112, 114 and 116 is obtained because the etching of the layer of sacrificial material 23 forms cavities, or air layers, 60 between the first dielectric layer 24 and the passivation layer 21. The suspended micro-bridge architecture from which the three devices 112, 114 and 116 benefit is advantageous since it forms an effective thermal insulation of the devices 112, 114 and 116 vis-à-vis the substrate 109, which improves the sensitivity of the matrix of infrared detectors 112 and the infrared sensor 114 on the one hand and the energy efficiency of the infrared emitter 116 on the other hand.

Each infrared detector of the matrix of infrared detectors 112 is formed, from bottom to top starting from the passivated surface of the circuit (the passivation layer 21), by a reflective metal film formed by the portion of reflective metal material 22, a layer of air or cavity 60 (corresponding to the space left free by the etching of the layer of sacrificial material 23) with a thickness of approximately 2.5 μm, a stack of layers comprising at least one resistive film formed by the portion 25c, the dielectric layers 24, 27 which are essentially transparent to the infrared wavelengths intended to be detected, and the thermoresistive transducer element formed by the portion 28c of temperature-sensitive material. In the matrix of infrared detectors 112, the resistive portion 25c is fragmented. Thus the portion of reflective metal material 22, the layer of air 60 and the fragmented portion 25c form a quarter-wave interferential cavity that has here a resonance peak at a wavelength $\lambda_1$, intended to be detected by the matrix of infrared detectors 112, for example equal to approximately 10 μm and which is therefore well suited for effecting a detection of activity of persons.

According to Maxwell's laws, this cavity 60 may be designed to obtain an absorption close to 100% at wavelengths equal to approximately 10 μm if the ratio (ρ/e) of the resistivity to the thickness of the portion 25c of the resistive layer 25 is around 120·π, that is to say approximately 377Ω, as described in the document U.S. Pat. No. 5,021,663. This electromagnetic impedance, or layer resistance, of 377Ω can be obtained from a resistive layer 25 comprising titanium nitride (TiN) deposited by reactive cathodic sputtering, with a resistivity of approximately 150 μΩ·cm, and a thickness of approximately 8 mm, and the portion 25c of which is fragmented so that its filling ratio (the surface area occupied by the metal of the portion 25c with respect to the total detection surface area of the infrared detector) is approximately 50%, in order to obtain an apparent resistivity of 300 μΩ·cm. The document U.S. Pat. No. 5,912,464 further describes that a fragmentation of a resistive film, such as the resistive layer 25, complies with design rules such that the pattern of the fragmented elements is repeated at a step lying typically between $\lambda_1$ and $0.5·\lambda_1$ in order to obtain a mean absorption greater than approximately 90%. The portion 25c may in this case be formed by bands of resistive material with a width equal to approximately 2.5 μm spaced apart by approximately 2.5 μm as far as bands with width of approximately 4 μm spaced apart by approximately 4 μm, for example in order to detect an infrared radiation with a wavelength of between approximately 8 μm and 12 μm.

Figure 3A:
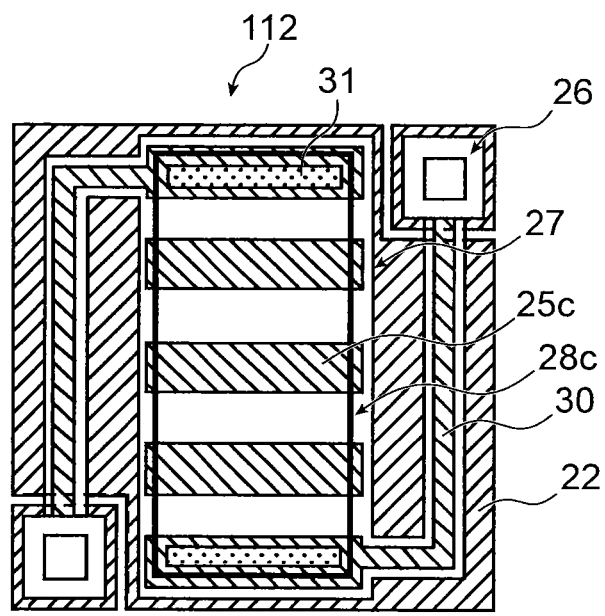
FIGS. 3a to 3c show plan views of elements of an infrared detection device according to a particular embodiment.

FIG. 3a shows by way of example a plan view of an infrared detector forming a pixel of the matrix of infrared detectors 112 produced as previously described. The absorption of the infrared rays by resistive coupling of the electrons of the portion 25c results in a temperature rise that propagates, by thermal coupling, through the second dielectric layer 27 as far as the portion 28c of temperature-sensitive material. The layer 28 may be produced from amorphous silicon, the resistivity/temperature coefficient pair of which can be adjusted over a wide range of values. A temperature coefficient of between approximately $-2\%·K^{-1}$ and $-4\%·K^{-1}$ may for example be obtained by a suitable doping of the amorphous silicon of the layer 28. By means of openings 31 produced through the second dielectric layer 27 during the step previously described in relation to FIG. 2e, the portion 28c (shown transparent in FIG. 3a) is electrically connected to at least two of the fragmented elements of metal of the portion 25c that are electrically connected to the portions of electrically conductive material 26 via the electrically conductive portions 30 with a reduced cross section, which enables the functional unit 1102 to measure the electrical resistance presented by the thermoresistive transducer formed by the portion 28c. The fragmented elements of the portion 25c are each for example substantially rectangular in shape and are aligned alongside one another. Other types of fragmented element may be produced, as described for example in the document U.S. Pat. No. 5,912, 464. The pixels of the matrix of infrared detectors 112 each comprising a thermal transducer, the sensitivity of the matrix of infrared detectors 112 is therefore improved because of the suspended structure of these detectors, which are therefore thermally isolated from the substrate 109. The thermal isolation is also increased because the suspended structure of the infrared detector is connected to the portions of electrically conductive material 26, by portions 30 of the resistive layer 25 with a reduced cross section. In addition, the thermal isolation may be further reinforced by causing the matrix of infrared detectors 112 to function under vacuum.

Figure 3B:
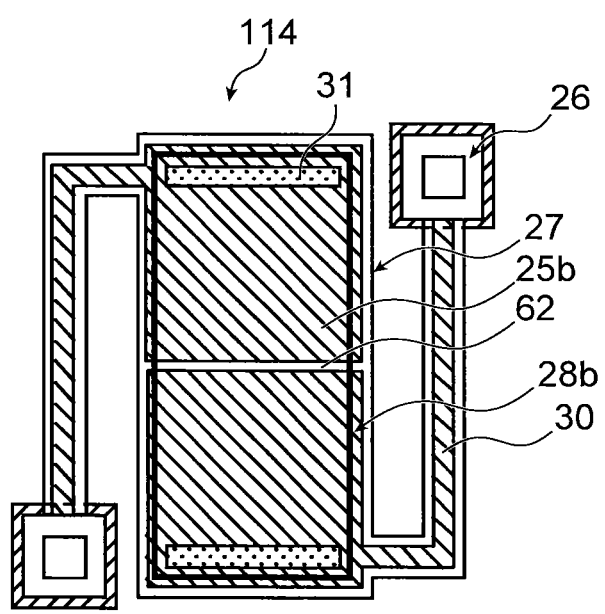

The infrared sensor 114 is essentially formed by the portion 25b of the resistive layer 25, surrounded by the dielectric layers 24, 27 and the portion 28b forming the thermoresistive transducer, the whole suspended in a purely dielectric environment. The infrared sensor 114 does not comprise any reflective metal material arranged on the passivation layer 21. In the infrared sensor 114, the portion 25b of the resistive layer 25 is essentially continuous, apart from a single cut out 62 produced at the etching step previously described in relation to FIG. 2d and the width of which (corresponding to the dimension separating the two parts of the portion 25b) is small compared with a wavelength $\lambda_2$ intended to be detected by the infrared sensor 114 and which is for example approximately 4.26 μm when the infrared sensor 114 is intended to detect $CO_2$. As shown in FIG. 3b (which shows a plan view of the infrared sensor 114), the cut out 62 divides the portion 25b into two elements with a substantially rectangular or square shape. According to Maxwell's laws, the absorption of a continuous resistive film separating two infinite dielectric half-spaces is approximately 50% whatever the wavelength absorbed, if the ratio (ρ/e) of the resistivity to the thickness of the resistive film is approximately 60·π, that is to say 188Ω, and on the assumption that the refractive index and the extinction coefficient of the resistive film are equal, which is generally the case in the field of infrared wavelengths. In the infrared sensor 114, a first upper half-space (situated above the portion 25b) is formed by the two layers 27, 28 and the space from which the infrared radiation comes, and a second lower half-space (situated below the portion 25b) is formed by the layer 24, the cavity 60, the layer 21 and the substrate 109 in which the lines of metal are preferably not integrated.

This electromagnetic impedance of 188Ω may be obtained from the same resistive layer 25 as that serving to form the portion 25c (for example composed of titanium nitride with a resistivity of approximately 150μΩ·cm, and a thickness of approximately 8 nm), but forming the portion 25b with a filling ratio of around 100%. The same provisions as those already described for the matrix of infrared detectors 112 may be adopted to couple the thermoresistive transducer 28b of the infrared sensor 114 and to connect it to the functional measuring unit 1104. The benefits afforded by a suspended construction and by functioning under vacuum previously described for the matrix of infrared detectors 112 are found again with the infrared sensor 114.

The infrared emitter 116 is essentially formed, from bottom to top starting from the passivation layer 21, from a reflective metal film formed by the portion of reflective metal material 22 (optional), a layer of air, or cavity, 60 with a height for example of approximately 2.5 μm, a stack of layers comprising at least the portion 25a of the resistive layer 25 surrounded by dielectric layers 24, 27 and covered by the portion 28a of temperature-sensitive material. The dielectric layers 24 and 27 serve respectively as a mechanical support and a protective layer for the portion 25a of the restive layer 25, which is the active element of the infrared emitter 116. During an emission of infrared radiation by the infrared emitter 116, the portion 25a is heated by dissipation of an electric current generated by the electronic circuit 10 (the functional unit 1106) and the control of which regulates both the temperature reached by the portion 25a and the radiative power that it emits. The suspended configuration provided for producing the infrared emitter 116 also improves the energy efficiency thereof (the ratio of the emitted radiative power to the dissipated Joule power). This is because a suspended configuration allied to a functioning under vacuum of the infrared emitter 116 isolates it thermally from the substrate 109 with a thermal impedance of a few $1.10^6$ k·$W^{-1}$. Under these conditions, a Joule dissipation of approximately 400 μW suffices to establish a temperature rise of 400° C. between the infrared source formed by the infrared emitter 116 and the substrate 109, the temperature of which is generally close to ambient temperature. This infrared source thus reaches a temperature of around 700 K which, according to Wien's law, corresponds to a blackbody emission peak at approximately 4.3 μm, consistent with the $CO_2$ absorption band. A Joule dissipation of 400 μW may be obtained using the same resistive layer 25, for example comprising titanium nitride (resistivity of approximately 150 μΩ·cm, thickness of approximately 8 nm), as that used for producing the infrared detector of the matrix 112 and the infrared sensor 114. For example, at the step of etching the resistive layer 25 shown in FIG. 2d, it is possible to etch the portion 25a in the form of a square in order to obtain an electrical resistance of 188Ω. Such a resistance makes it possible to dissipate approximately 400 μW at a biasing voltage of approximately 0.28 V with a current of approximately 1.45 mA.

Figure 3C:
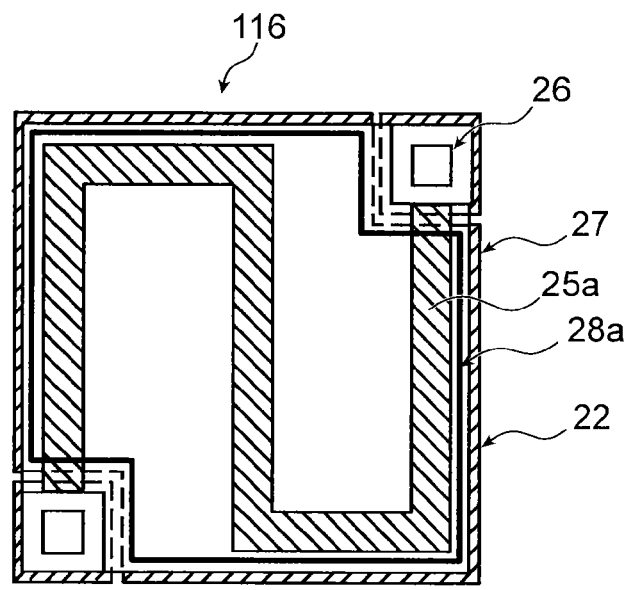

The portion 25a of the resistive layer 25 of the infrared emitter 116 may also be produced in the form of a rectangle or a coil (as shown in FIG. 3c), which makes it possible to achieve a power of approximately 400 μW but with a substantially higher resistance, and therefore better suited to the output impedance of the functional unit 1106 of the electronic circuit 110 that forms the control circuit of the infrared emitter 116. For example, the coil shown in FIG. 3c considered to be formed by approximately 35 squares of TiN connected in series along the pattern of the coil dissipates approximately 400 μW at approximately 1.6 V with a current of approximately 250 μA. The impedance matching between the portion 25a of the resistive layer 25 and the control circuit 1106 improves the energy efficiency of the infrared emitter 116. The presence of the portion 28a of temperature-sensitive material is optional and may be eliminated for example during the etching previously described in relation to FIG. 2e. This portion 28a of temperature-sensitive material however mechanically consolidates the layers 24, 25, 27, which are generally provided thin, in particular for reasons of thermal isolation of the infrared detectors of the matrix 112 and of the infrared sensor 114, and which would deform under the effect of the thermal expansion stresses introduced by heating thereof. Another advantage in preserving the portion 28a of temperature-sensitive material above the portion 25a of the resistive layer 25 is that it also contributes to the emission of the infrared flow of the infrared emitter 116.

The layer 28 comprises for example a semiconductor such as amorphous silicon, the electrical conductivity of which increase exponentially with the temperature. The activation of the infrared emitter 116 at a temperature of around 400° C. therefore fundamentally modifies the optical properties of the portion 28a, passing from essentially transparent at ambient temperature to greatly absorbent at high temperature, where the optical absorption properties of semiconductors are dictated by the high density of the free carriers. Under these conditions of high optical absorption, the infrared emission properties of the portion 28a are similar to those of a black body, which makes it possible to effectively cover the MWIR spectral range, and in particular the absorption bands of the main gases liable to be detected by the gas detection device 11 ($CO_2$, CO, etc).

Some of the radiative energy delivered by the infrared emitter 116 is emitted in the direction of the substrate 109. It is therefore advantageous to preserve a portion of reflective metal material 22 under the portion 25a of the infrared emitter 116 in order to return this energy upwards in the direction of the enclosure 125 where the gas or gases to be detected are situated, thus improving the energy efficiency of the infrared emitter 116. This also protects the electronic circuit 110 from the infrared radiation emitted by the infrared emitter 116 and therefore prevents excessive heating that would impair the stable functioning of the electronic circuit 110.

According to a variant of the production method previously described, it is possible for the geometry, in the plane (X;Y), of the portion 25b and/or the portion 25c to be essentially continuous as shown in FIG. 3b. In this case, it is the construction in the direction z of the infrared detectors of the matrix 112 and of the infrared sensor 114 that is individually adapted in order to obtain the required infrared absorption for the infrared detectors in the matrix 112 and of the infrared sensor 114, respectively in the LWIR band in the MWIR band, as described below.

Figure 4:
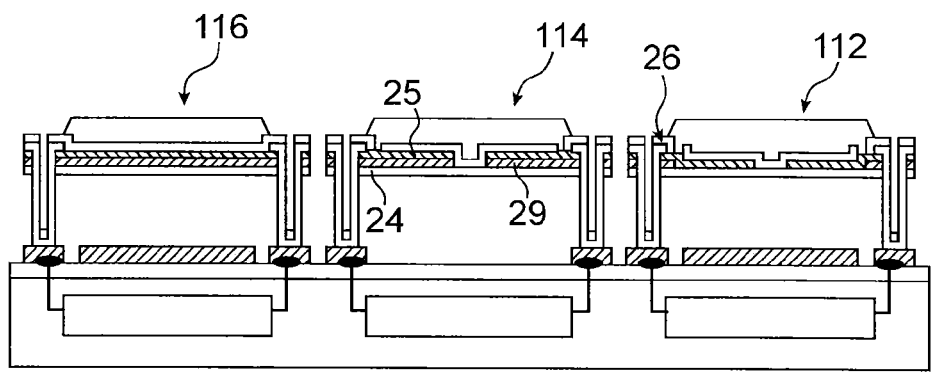

According to this variant, it is possible to provide the same geometry, in the plane (X;Y), of the portions 25c and 25b of the matrix of infrared detectors 112 and of the infrared sensor 114 so as to obtain the electromagnetic impedances sought for these infrared elements, respectively 377Ω and 188Ω. For this purpose, prior to the deposition of the resistive layer 25 on the first dielectric layer 24, a second resistive layer 29, for example metal or comprising doped semiconductor, is previously deposited on the dielectric layer 24, the resistive layer 25 next being deposited on this second resistive layer 29. At the matrix of infrared detectors 112, the second resistive layer 29 is eliminated, for example by photolithography and etching, prior to the deposition of the resistive layer 25, except at the electrical contacts formed by the portions of electrically conductive material 26 in order to guarantee good electrical contact. The resistive layers 25 and 29, composed of TiN and with a resistivity of approximately 150 μΩ·cm, are provided with a thinner thickness, for example equal to approximately 4 nm. The remainder of the method is unchanged, ensuring however, at the time of etching of the resistive layer 25, that both the resistive layer 25 and the second resistive layer 29 for the infrared sensor 114 and the infrared emitter 116 (FIG. 4) are etched.

As can be seen in FIGS. 2c to 2f and 4, the portions of electrically conductive material 26 extend between the portions 25a, 25b and 25c of the resistive layer 25 and the substrate 109, and form pillars mechanically supporting the portions 25a, 25b and 25c of the restive layer 25. The mechanical holding of the portions 25a, 25b and 25c of the resistive layer 25 above the substrate 109 may be provided only by the portions of electrically conductive material 26.

According to another variant embodiment, it is possible to add, on the surface of the layer 28 of temperature-sensitive material, an additional layer having properties of absorption in the first and second infrared ranges, for example LWIR and MWIR. Such a layer is for example produced from carbon nanotubes or composed of other materials such as carbon black or black gold (a material comprising high-porosity gold). The surface of this absorbent layer may also be covered with a thin protective layer, for example comprising $SiO_2$ and with a thickness of approximately 10 nm.

According to another variant embodiment, it is possible to etch the layer of reflective metal material 22 and the resistive layer 25 in the same pattern, for example essentially continuous, for the matrix of infrared detectors 112 and the infrared sensor 114. This variant is well suited to the case where the gas detection device 11 is intended to detect a gas having an infrared absorption band in the LWIR range.

It is also possible for the infrared sensor 114 to form part of the matrix of infrared detectors 112. In this case, the interferential filter enabling gas to be detected is offset outside the optical path of the infrared radiation carrying information on the activity of persons, that is to say outside the optical path of the matrix of infrared detectors, preferably in the enclosure 125.

In general terms, the resistivity of the resistive layer 25 may be different from 150 μΩ·cm, and its thickness is then adjusted accordingly in order to obtain the electromagnetic impedances of 377Ω and 188Ω required. This may be obtained for example by adjusting the parameters of the TiN deposition method elaborated by reactive sputtering, that is to say the parameters for deposition of the resistive layer 25. It is possible to obtain by this means a resistive layer having a resistivity for example lying between approximately 150 μΩ·cm and 750 μΩ·cm. Another possibility is producing the resistive layer 25 from materials other than TiN, for example $WSi_2$ or $MoSi_2$.

The invention claimed is:

1. An infrared detection device comprising
at least one gas detection device that comprises at least:
  a resistive layer, at least a first portion of which is able to emit a first infrared radiation in a first range of wavelengths able to be absorbed by the gas or gases to be detected, and at least a second portion of which is thermally coupled to at least one first element for the thermoresistive transduction of the first infrared radiation intended to be detected;
  a substrate comprising at least one first electronic circuit for controlling and reading the gas detection device;
  portions of electrically conductive material electrically connecting at least the first portion of the resistive layer and the first thermoresistive transduction element to the first electronic circuit, said portions of electrically conductive material mechanical holding of the first portion and second portion of the resistive layer opposite the substrate so that a distance between the first portion of the resistive layer and the substrate is substantially equal to a distance between the second portion of the resistive layer and the substrate;
the infrared detection device further comprising a matrix of infrared detectors such that each infrared detector comprises at least:
  a third portion of the resistive layer coupled thermally to at least a second element for the thermoresistive transduction of a second infrared radiation in a second range of wavelengths intended to be detected;
  portions of electrically conductive material electrically connecting the second thermoresistive transduction element to a second electronic circuit controlling and reading the matrix of infrared detectors implemented in the substrate, and providing mechanical holding of the third portion of the resistive element opposite the substrate such that a distance between the third portion of the resistive layer and the substrate is substantially equal to the distance between the second portion of the resistive layer and the substrate.

2. The device according to claim 1, in which each infrared detector also comprises at least one portion of reflective metal material arranged between the substrate and the third portion of the resistive layer of the infrared detector, the distance between the third portion of the resistive layer and the portion of reflective metal material, in each of the infrared detectors, being equal to approximately one quarter of a wavelength belonging to the second range of wavelengths and intended to be detected by the infrared detector.

3. The device according to claim 2, in which each of the third portions of the resistive layer comprises an electromagnetic impedance substantially equal to twice an electromagnetic impedance of the second portion of the resistive layer.

4. The device according to claim 1, in which the matrix of infrared detectors is optically coupled to an optical focusing system.

5. The device according to claim 1, also comprising at least one portion of material the resistivity of which is greater than that of the material of the resistive layer, arranged on the first portion of the resistive layer so that the first infrared radiation is intended to be emitted through said portion of material.

6. The device according to claim 5, wherein said portion of material the resistivity of which is greater than that of the material of the resistive layer comprises amorphous silicon.

7. The device according to claim 1, in which at least one of the first thermoresistive transduction element and the second thermoresistive transduction element comprises a first or a second portion of amorphous silicon.

8. The device according to claim 1, further comprising a housing in which at least one of the gas detection device and the matrix of infrared detectors is hermetically enclosed, the housing comprising at least one of a first portion of material transparent vis-à-vis the first range of wavelengths arranged opposite the gas detection device and a second portion of material transparent vis-à-vis the second range of wavelengths arranged opposite the matrix of infrared detectors.

9. The device according to claim 8, further comprising at least one of:
a first optical filter coupled to the first portion of material transparent vis-à-vis the first range of wavelengths and able to effect an optical filtering such that only the wavelengths intended to be absorbed by the gas or gases to be detected can pass through the first optical filter;
a second optical filter coupled to the second portion of material transparent vis-à-vis the second range of wavelengths and able to effect an optical filtering such that only the wavelengths of the second range of wavelengths can pass through the second optical filter.

10. The device according to claim 1, in which the restive layer comprises TiN and/or $MoSi_2$ and/or $WSi_2$.

11. The device according to claim 1, also comprising an optical reflection device arranged in an enclosure intended to contain the gas or gases to be detected and able to reflect the first infrared radiation emitted by the first portion of the resistive layer towards the second portion of the resistive layer.

12. The device according to claim 1, in which the resistive layer is such that the ratio of the resistivity of the material of the resistive layer to the thickness of the resistive layer is approximately 188 Ohms.

13. A method for producing an infrared detection device, comprising:
producing a gas detection device by:
providing a substrate having integrated therein at least one first electronic circuit configured to control and read the gas detection device;
depositing at least one layer of sacrificial material on the substrate;
depositing at least one resistive layer on the layer of sacrificial material;
etching the resistive layer and the layer of sacrificial material thereby forming at least one first portion of the resistive layer configured to emit a first infrared radiation in a first range of wavelengths to be absorbed by the gas or gases to detected, and forming at least one second portion of the resistive layer;
producing at least a first element for thermoresistive transduction of said first infrared radiation intended to be detected, the first thermoresistive transduction element being thermally coupled to the second portion of the resistive layer;
producing portions of electrically conductive material electrically connecting at least the first portion of the resistive layer and the first thermoresistive transduction element to the first electronic circuit respectively; and
eliminating the layer of sacrificial material by etching the layer of sacrificial material, wherein the portions of electrically conductive material providing a mechanical holding of the first portion and second portion of the resistive layer opposite the substrate such that a distance between the first portion of the resistive layer and the substrate is substantially equal to a distance between the second portion of the resistive layer and the substrate; and
producing a matrix of infrared detectors by:
etching the resistive layer so that it also forms a plurality of third portions of the resistive layer;
producing a plurality of second elements for the thermoresistive transduction of a second infrared radiation in a second range of wavelengths intended to be detected, each of the second thermoresistive transduction elements being thermally coupled to a respective one of the third portions of the resistive layer;
producing portions of electrically conductive material electrically connecting the second thermoresistive transduction elements to a second electronic circuit for controlling and reading the matrix of infrared detectors produced in the substrate; and providing mechanical holding of the third portions of the resistive layer opposite the substrate such that a distance between each of the third portions of the resistive layer and the substrate is substantially equal to the distance between the second portion of the resistive layer and the substrate.

14. The method according to claim 13, further comprising, before the deposition of the layer of sacrificial material on the substrate, the production, on the substrate, of portions of reflective metal material such that each portion of reflective metal material is arranged between the substrate and one of the third portions of the resistive layer, the distance between said one of the third portions of the resistive layer and said portion of reflective metal material being able to be equal to approximately one quarter of a wavelength belonging to the second range of wavelengths and intended to be detected by the matrix of infrared detectors.

* * * * *